US012065502B2

(12) United States Patent
Fast et al.

(10) Patent No.: US 12,065,502 B2
(45) Date of Patent: Aug. 20, 2024

(54) BISPECIFIC ANTIBODY FORMULATION

(71) Applicant: Hoffmann-La Roche Inc., Little Falls, NJ (US)

(72) Inventors: Jonas Fast, Basel (CH); Anja Sarah Paulus, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 819 days.

(21) Appl. No.: 16/750,646

(22) Filed: Jan. 23, 2020

(65) Prior Publication Data

US 2020/0231698 A1 Jul. 23, 2020

Related U.S. Application Data

(63) Continuation of application No. PCT/EP2018/070289, filed on Jul. 26, 2018.

(30) Foreign Application Priority Data

Jul. 28, 2017 (EP) .................................. 17183667

(51) Int. Cl.
| | | |
|---|---|---|
| *C07K 16/30* | (2006.01) | |
| *A61K 9/08* | (2006.01) | |
| *A61K 9/19* | (2006.01) | |
| *A61K 47/18* | (2017.01) | |
| *A61K 47/22* | (2006.01) | |
| *A61K 47/26* | (2006.01) | |
| *C07K 16/28* | (2006.01) | |

(52) U.S. Cl.
CPC ........ *C07K 16/3007* (2013.01); *A61K 47/183* (2013.01); *A61K 47/22* (2013.01); *A61K 47/26* (2013.01); *C07K 16/28* (2013.01); *C07K 16/2803* (2013.01); *C07K 16/2809* (2013.01); *A61K 9/08* (2013.01); *A61K 9/19* (2013.01); *C07K 2317/31* (2013.01); *C07K 2317/55* (2013.01)

(58) Field of Classification Search
CPC ............................ C07K 16/3007; C07K 16/28; C07K 16/2803; C07K 16/2809; C07K 2317/31; C07K 2317/55; A61K 9/08; A61K 9/19; A61K 47/183; A61K 47/22; A61K 47/26

See application file for complete search history.

(56) References Cited

U.S. PATENT DOCUMENTS

| | | | |
|---|---|---|---|
| 8,613,919 B1 * | 12/2013 | Ma .......................... | C07K 16/38 424/130.1 |
| 10,155,815 B2 | 12/2018 | Bacac et al. | |
| 10,781,257 B2 | 9/2020 | Bacac et al. | |
| 10,781,258 B2 | 9/2020 | Bacac et al. | |
| 2006/0088523 A1 | 4/2006 | Andya et al. | |
| 2011/0171125 A1 | 7/2011 | Elkins et al. | |
| 2014/0161817 A1 | 6/2014 | Siedler et al. | |
| 2014/0242079 A1 * | 8/2014 | Bacac ..................... | A61P 35/00 435/69.6 |
| 2016/0000916 A1 | 1/2016 | Crotts et al. | |
| 2016/0368985 A1 | 12/2016 | Hotzel et al. | |

FOREIGN PATENT DOCUMENTS

| | | |
|---|---|---|
| WO | 2014/131712 A1 | 9/2014 |
| WO | 2014/141712 A1 | 9/2014 |
| WO | 2016/036678 A1 | 3/2016 |
| WO | 2017/118675 A1 | 7/2017 |

OTHER PUBLICATIONS

Daugherty et al., "Formulation and delivery issues for monoclonal antibody therapeutics" Adv Drug Deliv Rev. 58:686-706 (2006).
International Preliminary Report on Patentability (IPRP) for PCT/EP2018/070289 issued on Jan. 28, 2020.
International Search Report for PCT/EP2018/070289 mailed on Sep. 28, 2018.
Ito et al., "Effects of subclass change on the structural stability of chimeric, humanized, and human antibodies under thermal stress" Protein Science 22(11):1542-1551 (2013).
Kang et al., "Rapid Formulation Development for Monoclonal Antibodies" BioProcess International 14(4):40-45 (2016).
Wang et al., "Antibody Structure, Instability, and Formulation" J. of Pharmaceutical Sciences 96(1):1-26 (2007).

\* cited by examiner

*Primary Examiner* — Kimberly Ballard
(74) *Attorney, Agent, or Firm* — Clark & Elbing LLP; Karen L. Elbing

(57) ABSTRACT

This invention relates to a pharmaceutical formulation of a bispecific antibody which binds to carcinoembryonic antigen (CEA) and CD3, a process for the preparation and uses of the formulation.

5 Claims, No Drawings
Specification includes a Sequence Listing.

SEQUENCE LISTING

<160> NUMBER OF SEQ ID NOS: 23

<210> SEQ ID NO 1
<211> LENGTH: 5
<212> TYPE: PRT
<213> ORGANISM: Artificial Sequence
<220> FEATURE:
<223> OTHER INFORMATION: CD3 HCDR1

<400> SEQUENCE: 1

Thr Tyr Ala Met Asn
1               5

<210> SEQ ID NO 2
<211> LENGTH: 19
<212> TYPE: PRT
<213> ORGANISM: Artificial Sequence
<220> FEATURE:
<223> OTHER INFORMATION: CD3 HCDR2

<400> SEQUENCE: 2

Arg Ile Arg Ser Lys Tyr Asn Asn Tyr Ala Thr Tyr Tyr Ala Asp Ser
1               5                   10                  15

Val Lys Gly

<210> SEQ ID NO 3
<211> LENGTH: 14
<212> TYPE: PRT
<213> ORGANISM: Artificial Sequence
<220> FEATURE:
<223> OTHER INFORMATION: CD3 HCDR3

<400> SEQUENCE: 3

His Gly Asn Phe Gly Asn Ser Tyr Val Ser Trp Phe Ala Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: CD3 LCDR1

<400> SEQUENCE: 4

Gly Ser Ser Thr Gly Ala Val Thr Thr Ser Asn Tyr Ala Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CD3 LCDR2

<400> SEQUENCE: 5

Gly Thr Asn Lys Arg Ala Pro
1               5

<210> SEQ ID NO 6
<211> LENGTH: 9
<212> TYPE: PRT
<213> ORGANISM: Artificial Sequence
<220> FEATURE:
<223> OTHER INFORMATION: CD3 LCDR3

<400> SEQUENCE: 6

-continued

```
Ala Leu Trp Tyr Ser Asn Leu Trp Val
1               5

<210> SEQ ID NO 7
<211> LENGTH: 125
<212> TYPE: PRT
<213> ORGANISM: Artificial Sequence
<220> FEATURE:
<223> OTHER INFORMATION: CD3 VH

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 8
<211> LENGTH: 109
<212> TYPE: PRT
<213> ORGANISM: Artificial Sequence
<220> FEATURE:
<223> OTHER INFORMATION: CD3 VL

<400> SEQUENCE: 8

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 9
<211> LENGTH: 5
<212> TYPE: PRT
<213> ORGANISM: Artificial Sequence
<220> FEATURE:
<223> OTHER INFORMATION: CEA HCDR1

<400> SEQUENCE: 9

Glu Phe Gly Met Asn
```

```
<210> SEQ ID NO 10
<211> LENGTH: 17
<212> TYPE: PRT
<213> ORGANISM: Artificial Sequence
<220> FEATURE:
<223> OTHER INFORMATION: CEA HCDR2

<400> SEQUENCE: 10

Trp Ile Asn Thr Lys Thr Gly Glu Ala Thr Tyr Val Glu Glu Phe Lys
1               5                   10                  15
Gly

<210> SEQ ID NO 11
<211> LENGTH: 12
<212> TYPE: PRT
<213> ORGANISM: Artificial Sequence
<220> FEATURE:
<223> OTHER INFORMATION: CEA HCDR3

<400> SEQUENCE: 11

Trp Asp Phe Ala Tyr Tyr Val Glu Ala Met Asp Tyr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: CEA LCDR1

<400> SEQUENCE: 12

Lys Ala Ser Ala Ala Val Gly Thr Tyr Val Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: CEA LCDR2

<400> SEQUENCE: 13

Ser Ala Ser Tyr Arg Lys Arg
1               5

<210> SEQ ID NO 14
<211> LENGTH: 10
<212> TYPE: PRT
<213> ORGANISM: Artificial Sequence
<220> FEATURE:
<223> OTHER INFORMATION: CEA LCDR3

<400> SEQUENCE: 14

His Gln Tyr Tyr Thr Tyr Pro Leu Phe Thr
1               5                   10

<210> SEQ ID NO 15
<211> LENGTH: 121
<212> TYPE: PRT
<213> ORGANISM: Artificial Sequence
<220> FEATURE:
<223> OTHER INFORMATION: CEA VH

<400> SEQUENCE: 15
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser
            115                 120

<210> SEQ ID NO 16
<211> LENGTH: 108
<212> TYPE: PRT
<213> ORGANISM: Artificial Sequence
<220> FEATURE:
<223> OTHER INFORMATION: CEA VL

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys
            100                 105

<210> SEQ ID NO 17
<211> LENGTH: 215
<212> TYPE: PRT
<213> ORGANISM: Artificial Sequence
<220> FEATURE:
<223> OTHER INFORMATION: CEA CD3 bsAb LC(CEA)

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 18
<211> LENGTH: 214
<212> TYPE: PRT
<213> ORGANISM: Artificial Sequence
<220> FEATURE:
<223> OTHER INFORMATION: CEA CD3 bsAb LC(CD3)

<400> SEQUENCE: 18

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210
```

<210> SEQ ID NO 19
<211> LENGTH: 694
<212> TYPE: PRT
<213> ORGANISM: Artificial Sequence
<220> FEATURE:
<223> OTHER INFORMATION: CEA CD3 bsAB HC(CEA-CD3-Fc)

<400> SEQUENCE: 19

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Gly Gly Gly Ser Gly Gly Gly Ser Glu Val Gln Leu Leu
225                 230                 235                 240

Glu Ser Gly Gly Gly Leu Val Gln Pro Gly Gly Ser Leu Arg Leu Ser
                245                 250                 255

Cys Ala Ala Ser Gly Phe Thr Phe Ser Thr Tyr Ala Met Asn Trp Val
            260                 265                 270

Arg Gln Ala Pro Gly Lys Gly Leu Glu Trp Val Ser Arg Ile Arg Ser
        275                 280                 285

Lys Tyr Asn Asn Tyr Ala Thr Tyr Tyr Ala Asp Ser Val Lys Gly Arg
    290                 295                 300

Phe Thr Ile Ser Arg Asp Asp Ser Lys Asn Thr Leu Tyr Leu Gln Met
305                 310                 315                 320

Asn Ser Leu Arg Ala Glu Asp Thr Ala Val Tyr Tyr Cys Val Arg His
                325                 330                 335

Gly Asn Phe Gly Asn Ser Tyr Val Ser Trp Phe Ala Tyr Trp Gly Gln
            340                 345                 350

Gly Thr Leu Val Thr Val Ser Ser Ala Ser Val Ala Ala Pro Ser Val
        355                 360                 365
```

Phe Ile Phe Pro Pro Ser Asp Glu Gln Leu Lys Ser Gly Thr Ala Ser
            370                 375                 380

Val Val Cys Leu Leu Asn Asn Phe Tyr Pro Arg Glu Ala Lys Val Gln
385                 390                 395                 400

Trp Lys Val Asp Asn Ala Leu Gln Ser Gly Asn Ser Gln Glu Ser Val
                405                 410                 415

Thr Glu Gln Asp Ser Lys Asp Ser Thr Tyr Ser Leu Ser Ser Thr Leu
            420                 425                 430

Thr Leu Ser Lys Ala Asp Tyr Glu Lys His Lys Val Tyr Ala Cys Glu
        435                 440                 445

Val Thr His Gln Gly Leu Ser Ser Pro Val Thr Lys Ser Phe Asn Arg
450                 455                 460

Gly Glu Cys Asp Lys Thr His Thr Cys Pro Pro Cys Pro Ala Pro Glu
465                 470                 475                 480

Ala Ala Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
            500                 505                 510

Val Ser His Glu Asp Pro Glu Val Lys Phe Asn Trp Tyr Val Asp Gly
        515                 520                 525

Val Glu Val His Asn Ala Lys Thr Lys Pro Arg Glu Glu Gln Tyr Asn
530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Gly
                565                 570                 575

Ala Pro Ile Glu Lys Thr Ile Ser Lys Ala Lys Gly Gln Pro Arg Glu
            580                 585                 590

Pro Gln Val Tyr Thr Leu Pro Pro Cys Arg Asp Glu Leu Thr Lys Asn
        595                 600                 605

Gln Val Ser Leu Trp Cys Leu Val Lys Gly Phe Tyr Pro Ser Asp Ile
610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
            660                 665                 670

Ser Val Met His Glu Ala Leu His Asn His Tyr Thr Gln Lys Ser Leu
        675                 680                 685

Ser Leu Ser Pro Gly Lys
    690

<210> SEQ ID NO 20
<211> LENGTH: 451
<212> TYPE: PRT
<213> ORGANISM: Artificial Sequence
<220> FEATURE:
<223> OTHER INFORMATION: CEA CD3 bsAB HC(CEA-Fc)

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

```
Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
 50                  55                  60

Lys Gly Arg Val Thr Phe Thr Asp Thr Ser Thr Ser Thr Ala Tyr
 65                  70                  75                  80

Met Glu Leu Arg Ser Leu Arg Ser Asp Thr Ala Val Tyr Tyr Cys
                85                  90                  95

Ala Arg Trp Asp Phe Ala Tyr Tyr Val Glu Ala Met Asp Tyr Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
    355                 360                 365

Leu Ser Cys Ala Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
    435                 440                 445
```

Pro Gly Lys
    450

<210> SEQ ID NO 21
<211> LENGTH: 225
<212> TYPE: PRT
<213> ORGANISM: Homo sapiens

<400> SEQUENCE: 21

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 22
<211> LENGTH: 207
<212> TYPE: PRT
<213> ORGANISM: Homo sapiens

<400> SEQUENCE: 22

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

```
His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
            195                 200                 205

<210> SEQ ID NO 23
<211> LENGTH: 198
<212> TYPE: PRT
<213> ORGANISM: Macaca fascicularis

<400> SEQUENCE: 23

Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
            20                  25                  30

Gln Thr Pro Tyr Gln Val Ser Ile Ser Gly Thr Thr Val Ile Leu Thr
        35                  40                  45

Cys Ser Gln His Leu Gly Ser Glu Ala Gln Trp Gln His Asn Gly Lys
    50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                85                  90                  95

Glu Asp Ala Ser His His Leu Tyr Leu Lys Ala Arg Val Cys Glu Asn
            100                 105                 110

Cys Met Glu Met Asp Val Met Ala Val Ala Thr Ile Val Ile Val Asp
            115                 120                 125

Ile Cys Ile Thr Leu Gly Leu Leu Leu Val Tyr Tyr Trp Ser Lys
130                 135                 140

Asn Arg Lys Ala Lys Ala Lys Pro Val Thr Arg Gly Ala Gly Ala Gly
145                 150                 155                 160

Gly Arg Gln Arg Gly Gln Asn Lys Glu Arg Pro Pro Val Pro Asn
                165                 170                 175

Pro Asp Tyr Glu Pro Ile Arg Lys Gly Gln Gln Asp Leu Tyr Ser Gly
            180                 185                 190

Leu Asn Gln Arg Arg Ile
            195
```

BISPECIFIC ANTIBODY FORMULATION

CROSS REFERENCE TO RELATED APPLICATIONS

This application is a continuation of International Application No. PCT/EP2018/070289, filed July 26, 2018, the entire contents of which is incorporated herein by reference, and which claims benefit to European Patent Application No. 17183667.9, filed July 28, 2017.

SEQUENCE LISTING

This application contains a Sequence Listing, which has been submitted electronically via EFS-Web in ASCII format and is hereby incorporated by reference in its entirety. Said ASCII copy, created on January 21, 2020, is named P34356-US_sequence_listing.txt and is 26,491 bytes in size.

DETAILED DESCRIPTION

The present invention relates to a pharmaceutical formulation of a bispecific antibody which binds to carcinoembryonic antigen (CEA) and CD3 (CEA CD3 bispecific antibody), a process for the preparation of the formulation and uses of the formulation.

Unless otherwise defined in the following, terms are used herein as generally used in the art.

In a first aspect, the invention relates to a pharmaceutical formulation comprising:
1 to 200 mg/ml of a CEA CD3 bispecific antibody;
1 to 100 mM of a buffering agent;
0.001 to 1% (w/v) of a surfactant;
1 to 500 mM of at least one stabilizer;
at a pH in the range of from 4.0 to 7.0.

The formulation according to the invention may be provided in liquid form, lyophilized form or in liquid form reconstituted from a lyophilized form.

CEA CD3 bispecific antibodies useful in the formulation according to the present invention are described in detail hereinbelow.

In a preferred embodiment, the concentration of the CEA CD3 bispecific antibody comprised in the formulation according to the invention is in the range of 1 to 100 mg/ml, preferably 10 to 75 mg/ml, most preferably 20 to 50 mg/ml. Particularly preferred is a concentration of 50 mg/ml. In some embodiments, the concentration of the CEA CD3 bispecific antibody comprised in the formulation is 5 mg/ml.

The term "buffering agent" as used herein denotes a pharmaceutically acceptable excipient, which stabilizes the pH of a pharmaceutical preparation. Suitable buffers are well known in the art and can be found in the literature. For example, citrate salts, acetate salts, histidine salts, succinate salts, malate salts, phosphate salts or lactate salts, and/or the respective free acids or bases thereof, as well as mixtures of the various salts and/or acids and bases thereof can be employed. Preferred pharmaceutically acceptable buffers comprise but are not limited to histidine buffers, citrate buffers, succinate buffers, acetate buffers and phosphate buffers. Preferred buffers for use in the present invention are histidine buffers, i.e. buffers having histidine, generally L-histidine, as buffering agent. Most preferred is L-histidine/HCl buffer, comprising L-histidine or mixtures of L-histidine and L-histidine hydrochloride and pH adjustment achieved with hydrochloric acid. Unless otherwise indicated, the term "L-histidine" when used herein to describe a buffering agent, refers to L-histidine/HCl buffer. L-histidine/HCl buffer can be prepared by dissolving suitable amounts of L-histidine and L-histidine hydrochloride in water, or by dissolving a suitable amount of L-histidine in water and adjusting the pH to the desired value by addition of hydrochloric acid. The abovementioned buffers are generally used at a concentration of about 1 mM to about 100 mM, preferably of about 10 mM to about 50 mM, more preferably of about 15 to 30 mM, and most preferably of 20 mM. Regardless of the buffer used, the pH can be adjusted to a value in the range from about 4.0 to about 7.0, preferably about 5.0 to about 6.0, and most preferably about 5.5, with an acid or a base known in the art, e.g. hydrochloric acid, acetic acid, phosphoric acid, sulfuric acid and citric acid, sodium hydroxide and potassium hydroxide.

The term "surfactant" as used herein denotes a pharmaceutically acceptable, surface-active agent. Preferably, a non-ionic surfactant is used. Examples of pharmaceutically acceptable surfactants include, but are not limited to, polyoxyethylen-sorbitan fatty acid esters (Tween), polyoxyethylene alkyl ethers (Brij), alkylphenylpolyoxyethylene ethers (Triton X), polyoxyethylene-polyoxypropylene copolymers (Poloxamer, Pluronic), and sodium dodecyl sulphate (SDS). Preferred polyoxyethylene-sorbitan fatty acid esters are polysorbate 20 (polyoxyethylene sorbitan monolaureate, sold under the trademark Tween 20™) and polysorbate 80 (polyoxyethylene sorbitan monooleate, sold under the trademark Tween 80™). Preferred polyethylene-polypropylene copolymers are those sold under the names Pluronic® F68 or Poloxamer 188™. Preferred polyoxyethylene alkyl ethers are those sold under the trademark Brij™. Preferred alkylphenylpolyoxyethylene ethers are sold under the tradename Triton X, most preferred is p-tert-octylphenoxy polyethoxyethanol (sold under the tradename Triton X-100™). Preferred surfactants for use in the present invention are polyoxyethylen-sorbitan fatty acid esters, preferably polysorbate 20 or polysorbate 80, most preferably polysorbate 20. When polysorbate 20 (Tween 20™) and polysorbate 80 (Tween 80™) are used, they are generally used at a concentration range of about 0.001 to about 1%, preferably of about 0.01 to about 0.1%, more preferably of about 0.02% to about 0.05%, most preferably of about 0.05%. In the formulation of the invention, the concentration of the surfactant is described as a percentage, expressed in weight/volume (w/v).

The term "stabilizer" as used herein denotes a pharmaceutically acceptable excipient, which protects the active pharmaceutical ingredient and/or the formulation from chemical and/or physical degradation during manufacturing, storage and application. Stabilizers include but are not limited to saccharides, amino acids, polyols (e.g. mannitol, sorbitol, xylitol, dextran, glycerol, arabitol, propylene glycol, polyethylene glycol), cyclodextrines (e.g. hydroxypropyl-β-cyclodextrine, sulfobutylethyl-(3-cyclodextrine, p-cyclodextrine), polyethylenglycols (e.g. PEG 3000, PEG 3350, PEG 4000, PEG 6000), albumines (e.g. human serum albumin (HSA), bovine serum albumin (BSA)), salts (e.g. sodium chloride, magnesium chloride, calcium chloride), chelators (e.g. EDTA) as hereafter defined. As mentioned hereinabove, stabilizers can be present in the formulation in an amount of about 1 to about 500 mM, preferably in an amount of about 10 to about 300 mM and more preferably in an amount of about 120 mM to about 300 mM. More than one stabilizer, selected from the same or from different groups, can be present in the formulation.

The term "saccharide" as used herein includes monosaccharides and oligosaccharides. A monosaccharide is a monomeric carbohydrate which is not hydrolysable by acids, including simple sugars and their derivatives, e.g. amino-sugars. Saccharides are usually in their D conformation. Examples of monosaccharides include glucose, fructose, galactose, mannose, sorbose, ribose, deoxyribose, neuraminic acid. An oligosaccharide is a carbohydrate consisting of more than one monomeric saccharide unit connected via glycosidic bond(s) either branched or in a linear chain. The monomeric saccharide units within an oligosaccharide can be identical or different. Depending on the number of monomeric saccharide units the oligosaccharide is a di-, tri-, tetra- penta- and so forth saccharide. In contrast to polysaccharides the monosaccharides and oligosaccharides are water soluble. Examples of oligosaccharides include sucrose, trehalose, lactose, maltose and raffinose. Preferred saccharides for use in the present invention are sucrose and trehalose (i.e. α,α-D-trehalose), most preferred is sucrose. Trehalose is available as trehalose dihydrate. Saccharides can be present in the formulation in an amount of about 100 to about 500 mM, preferably in an amount of about 200 to about 300 mM, more preferably in an amount of about 220 to about 250 mM, particularly an amount of about 230 mM or about 240 mM, most preferably in an amount of about 230 mM.

The term "amino acid" as used herein denotes a pharmaceutically acceptable organic molecule possessing an amino moiety located at a-position to a carboxylic group. Examples of amino acids include but are not limited to arginine, glycine, ornithine, lysine, histidine, glutamic acid, asparagic acid, isoleucine, leucine, alanine, phenylalanine, tyrosine, tryptophane, methionine, serine, proline. The amino acid employed is preferably in each case the L-form. Basic amino acids, such as arginine, histidine, or lysine, are preferably employed in the form of their inorganic salts (advantageously in the form of the hydrochloric acid salts, i.e. as amino acid hydrochlorides). A preferred amino acid for use in the present invention is methionine. Methionine is preferably used at a concentration of about 5 to about 25 mM, most preferably about 10 mM.

A subgroup within the stabilizers are lyoprotectants. The term "lyoprotectant" denotes pharmaceutically acceptable excipients, which protect the labile active ingredient (e.g. a protein) against destabilizing conditions during the lyophilisation process, subsequent storage and reconstitution. Lyoprotectants comprise but are not limited to the group consisting of saccharides, polyols (such as e.g. sugar alcohols) and amino acids. Preferred lyoprotectants can be selected from the group consisting of saccharides such as sucrose, trehalose, lactose, glucose, mannose, maltose, galactose, fructose, sorbose, raffinose, neuraminic acid, amino sugars such as glucosamine, galactosamine, N-methylglucosamine ("Meglumine"), polyols such as mannitol and sorbitol, and amino acids such as arginine and glycine or mixtures thereof. Lyoprotectants are generally used in an amount of about 10 to 500 mM, preferably in an amount of about 10 to about 300 mM and more preferably in an amount of about 100 to about 300 mM.

A subgroup within the stabilizers are antioxidants. The term "antioxidant" denotes pharmaceutically acceptable excipients, which prevent oxidation of the active pharmaceutical ingredient. Antioxidants comprise but are not limited to ascorbic acid, gluthathione, cysteine, methionine, citric acid, EDTA. Antioxidants can be used in an amount of about 0.01 to about 100 mM, preferably in an amount of about 5 to about 50 mM and more preferably in an amount of about 5 to about 25 mM.

The formulations according to the invention may also comprise one or more tonicity agents. The term "tonicity agents" denotes pharmaceutically acceptable excipients used to modulate the tonicity of the formulation. The formulation can be hypotonic, isotonic or hypertonic. Isotonicity in general relates to the osmotic pressure of a solution, usually relative to that of human blood serum (around 250-350 mOsmol/kg). The formulation according to the invention can be hypotonic, isotonic or hypertonic but will preferably be isotonic. An isotonic formulation is liquid or liquid reconstituted from a solid form, e.g. from a lyophilized form, and denotes a solution having the same tonicity as some other solution with which it is compared, such as physiologic salt solution and the blood serum. Suitable tonicity agents comprise but are not limited to sodium chloride, potassium chloride, glycerine and any component from the group of amino acids or sugars, in particular glucose. Tonicity agents are generally used in an amount of about 5 mM to about 500 mM.

Within the stabilizers and tonicity agents there is a group of compounds which can function in both ways, i.e. they can at the same time be a stabilizer and a tonicity agent. Examples thereof can be found in the group of sugars, amino acids, polyols, cyclodextrines, polyethyleneglycols and salts. An example for a sugar which can at the same time be a stabilizer and a tonicity agent is trehalose.

The formulations may also contain adjuvants such as preservatives, wetting agents, emulsifying agents and dispersing agents. Prevention of presence of microorganisms may be ensured both by sterilization procedures, and by the inclusion of various antibacterial and antifungal agents, e.g. paraben, chlorobutanol, phenol, sorbic acid, and the like. Preservatives are generally used in an amount of about 0.001 to about 2% (w/v). Preservatives comprise but are not limited to ethanol, benzyl alcohol, phenol, m-cresol, p-chlor-m-cresol, methyl or propyl parabens, benzalkonium chloride.

The CEA CD3 bispecific antibody comprised in the formulation according to the invention is a bispecific antibody that specifically binds to CD3 and to CEA. Particularly useful CEA CD3 bispecific antibodies are described e.g. in PCT publication no. WO 2014/131712 (incorporated herein by reference in its entirety).

The term "bispecific" means that the antibody is able to specifically bind to at least two distinct antigenic determinants. Typically, a bispecific antibody comprises two antigen binding sites, each of which is specific for a different antigenic determinant. In certain embodiments the bispecific antibody is capable of simultaneously binding two antigenic determinants, particularly two antigenic determinants expressed on two distinct cells.

As used herein, the term "antigenic determinant" is synonymous with "antigen" and "epitope", and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM).

As used herein, the term "antigen binding moiety" refers to a polypeptide molecule that specifically binds to an antigenic determinant. In one embodiment, an antigen binding moiety is able to direct the entity to which it is attached (e.g. a second antigen binding moiety) to a target site, for example to a specific type of tumor cell bearing the antigenic determinant. In another embodiment an antigen binding moiety is able to activate signaling through its target antigen, for example a T cell receptor complex antigen. Antigen binding moieties include antibodies and fragments thereof as further defined herein. Particular antigen binding moieties include an antigen binding domain of an antibody, comprising an antibody heavy chain variable region and an antibody light chain variable region. In certain embodiments, the antigen binding moieties may comprise antibody constant regions as further defined herein and known in the art. Useful heavy chain constant regions include any of the five isotypes: α, δ, ε, γ, or μ. Useful light chain constant regions include any of the two isotypes: κ and λ.

By "specific binding" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance (SPR) technique (analyzed e.g. on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an antibody comprising that antigen binding moiety, has a dissociation constant ($K_D$) of ≤1 μM, ≤100 nM, ≤10 nM, ≤1 nM, ≤0.1 nM, ≤0.01 nM, or ≤0.001 nM (e.g. 10 μM or less, e.g. from $10^{-8}$ M to $10^{-13}$ M e.g., from $10^{-9}$ M to $10^{-13}$ M).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen, or a receptor and its ligand). The affinity of a molecule X for its partner Y can generally be represented by the dissociation constant (KD), which is the ratio of dissociation and association rate constants ($k_{off}$ and $k_{on}$, respectively). Thus, equivalent affinities may comprise different rate constants, as long as the ratio of the rate constants remains the same. Affinity can be measured by well established methods known in the art, including those described herein. A particular method for measuring affinity is Surface Plasmon Resonance (SPR).

"CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In one embodiment, CD3 is human CD3, particularly the epsilon subunit of human CD3 (CD3ε). The amino acid sequence of human CD3ε is shown in UniProt (www.uniprot.org) accession no. P07766 (version 144), or NCBI (www.ncbi.nlm.nih.gov/) RefSeq NP 000724.1. See also SEQ ID NO: 22. The amino acid sequence of cynomolgus [Macaca fascicularis] CD3ε is shown in NCBI GenBank no. BAB71849.1. See also SEQ ID NO: 23.

"Carcinoembryonic antigen" or "CEA" (also known as Carcinoembryonic antigen-related cell adhesion molecule 5 (CEACAM5)) refers to any native CEA from any vertebrate source, including mammals such as primates (e.g. humans), non-human primates (e.g. cynomolgus monkeys) and rodents (e.g. mice and rats), unless otherwise indicated. The term encompasses "full-length," unprocessed CEA as well as any form of CEA that results from processing in the cell. The term also encompasses naturally occurring variants of CEA, e.g., splice variants or allelic variants. In one embodiment, CEA is human CEA. The amino acid sequence of human CEA is shown in UniProt (www.uniprot.org) accession no. P06731, or NCBI (www.ncbi.nlm.nih.gov/) RefSeq NP_004354.2.

As used herein, the terms "first", "second" or "third" with respect to Fab molecules etc., are used for convenience of distinguishing when there is more than one of each type of moiety. Use of these terms is not intended to confer a specific order or orientation of the bispecific antibody unless explicitly so stated.

The term "valent" as used herein denotes the presence of a specified number of antigen binding sites in an antibody. As such, the term "monovalent binding to an antigen" denotes the presence of one (and not more than one) antigen binding site specific for the antigen in the antibody.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity.

The terms "full length antibody," "intact antibody," and "whole antibody" are used herein interchangeably to refer to an antibody having a structure substantially similar to a native antibody structure.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W. H. Freeman and Co., page 91 (2007). A single VH or VL domain may be sufficient to confer antigen-binding specificity. As used herein in connection with variable region sequences, "Kabat numbering" refers to the numbering system set forth by Kabat et al., *Sequences of Proteins of Immunological Interest*, 5th Ed. Public Health Service, National Institutes of Health, Bethesda, MD (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991), referred to as "numbering according to Kabat" or "Kabat numbering" herein. Specifically the Kabat numbering system (see pages 647-660 of Kabat, et al., Sequences of Proteins of Immunological Interest, 5th ed., Public Health Service, National Institutes of Health, Bethesda, MD (1991)) is used for the light chain constant domain CL of kappa and lambda isotype and the Kabat EU index numbering system (see pages 661-723) is used for the heavy chain constant domains (CH1, Hinge, CH2 and CH3), which is herein further clarified by referring to "numbering according to Kabat EU index" in this case.

The term "hypervariable region" or "HVR", as used herein, refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs; three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following order in VH (or VL): FR1-H1(L1)-FR2-H2(L2)-FR3-H3(L3)-FR4.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, IgG3, IgG4, IgAi, and IgA2. The heavy chain constant domains that correspond to the different classes of immunoglobulins are called $\alpha$, $\delta$, $\varepsilon$, $\gamma$, and $\mu$, respectively.

A "Fab molecule" refers to a protein consisting of the VH and CH1 domain of the heavy chain (the "Fab heavy chain") and the VL and CL domain of the light chain (the "Fab light chain") of an immunoglobulin.

By a "crossover" Fab molecule (also termed "Crossfab") is meant a Fab molecule wherein the variable domains or the constant domains of the Fab heavy and light chain are exchanged (i.e. replaced by each other), i.e. the crossover Fab molecule comprises a peptide chain composed of the light chain variable domain VL and the heavy chain constant domain 1 CH1 (VL-CH1, in N- to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CH1 is lreferred to herein as the "heavy chain" of the (crossover) Fab molecule. Conversely, in a crossover Fab molecule wherein the constant domains of the Fab light chain and the Fab heavy chain are exchanged, the peptide chain comprising the heavy chain variable domain VH is referred to herein as the "heavy chain" of the (crossover) Fab molecule.

In contrast thereto, by a "conventional" Fab molecule is meant a Fab molecule in its natural format, i.e. comprising a heavy chain composed of the heavy chain variable and constant domains (VH-CH1, in N- to C-terminal direction), and a light chain composed of the light chain variable and constant domains (VL-CL, in N- to C-terminal direction).

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable domain (VH), also called a variable heavy domain or a heavy chain variable region, followed by three constant domains (CH1, CH2, and CH3), also called a heavy chain constant region. Similarly, from N- to C-terminus, each light chain has a variable domain (VL), also called a variable light domain or a light chain variable region, followed by a constant light (CL) domain, also called a light chain constant region. The heavy chain of an immunoglobulin may be assigned to one of five types, called $\alpha$ (IgA), $\delta$ (IgD), $\varepsilon$ (IgE), $\gamma$ (IgG), or $\mu$ (IgM), some of which may be further divided into subtypes, e.g. $\gamma_1$ ($IgG_1$), $\gamma_2$ ($IgG_2$), $\gamma_3$ ($IgG_3$), $\gamma4$ ($IgG_4$), $\alpha_1$ (IgAi) and $\alpha_2$ ($IgA_2$). The light chain of an immunoglobulin may be assigned to one of two types, called kappa ($\kappa$) and lambda ($\lambda$), based on the amino acid sequence of its constant domain. An immunoglobulin essentially consists of two Fab molecules and an Fc domain, linked via the immunoglobulin hinge region.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, antibodies produced by host cells may undergo post-translational cleavage of one or more, particularly one or two, amino acids from the C-terminus of the heavy chain.

Therefore an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (K447), of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. For purposes herein, however, % amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227- 258; and Pearson et. al. (1997) Genomics 46:24-36, and is publicly available from http://fasta.bioch.virginia.edu/fasta www2/fasta down.shtml. Alternatively, a public server accessible at http://fasta.bioch.virginia.edu/fasta www2/index.cgi can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcγRI (CD89).

"Reduced binding", for example reduced binding to an Fc receptor, refers to a decrease in affinity for the respective interaction, as measured for example by SPR. For clarity, the term includes also reduction of the affinity to zero (or below the detection limit of the analytic method), i.e. complete abolishment of the interaction. Conversely, "increased binding" refers to an increase in binding affinity for the respective interaction.

By "fused" is meant that the components (e.g. a Fab molecule and an Fc domain subunit) are linked by peptide bonds, either directly or via one or more peptide linkers.

The CEA CD3 bispecific antibody comprises a first antigen binding moiety that specifically binds to CD3, and a second antigen binding moiety that specifically binds to CEA.

In one embodiment, the first antigen binding moiety comprises a heavy chain variable region comprising the heavy chain CDR (HCDR) 1 of SEQ ID NO: 1, the HCDR2 of SEQ ID NO: 2, and the HCDR3 of SEQ ID NO: 3; and a light chain variable region comprising the light chain CDR (LCDR) 1 of SEQ ID NO: 4, the LCDR2 of SEQ ID NO: 5 and the LCDR3 of SEQ ID NO: 6.

In one embodiment, the second antigen binding moiety comprises a heavy chain variable region comprising the heavy chain CDR (HCDR) 1 of SEQ ID NO: 9, the HCDR2 of SEQ ID NO: 10, and the HCDR3 of SEQ ID NO: 11; and a light chain variable region comprising the light chain CDR (LCDR) 1 of SEQ ID NO: 12, the LCDR2 of SEQ ID NO: 13 and the LCDR3 of SEQ ID NO: 14.

In a particular embodiment, the CEA CD3 bispecific antibody comprises
(i) a first antigen binding moiety that specifically binds to CD3 and comprises a heavy chain variable region comprising the heavy chain CDR (HCDR) 1 of SEQ ID NO: 1, the HCDR2 of SEQ ID NO: 2, and the HCDR3 of SEQ ID NO: 3; and a light chain variable region comprising the light chain CDR (LCDR) 1 of SEQ ID NO: 4, the LCDR2 of SEQ ID NO: 5 and the LCDR3 of SEQ ID NO: 6; and (ii) a second antigen binding moiety that specifically binds to CEA and comprises a heavy chain variable region comprising the heavy chain CDR (HCDR) 1 of SEQ ID NO: 9, the HCDR2 of SEQ ID NO: 10, and the HCDR3 of SEQ ID NO: 11; and a light chain variable region comprising the light chain CDR (LCDR) 1 of SEQ ID NO: 12, the LCDR2 of SEQ ID NO: 13 and the LCDR3 of SEQ ID NO: 14.

In one embodiment, the first antigen binding moiety comprises a heavy chain variable region sequence that is at least about 95%, 96%, 97%, 98%, 99% or 100% identical to the amino acid sequence of SEQ ID NO: 7 and a light chain variable region sequence that is at least about 95%, 96%, 97%, 98%, 99% or 100% identical to the amino acid sequence of SEQ ID NO: 8.

In one embodiment, the first antigen binding moiety comprises the heavy chain variable region sequence of SEQ ID NO: 7 and the light chain variable region sequence of SEQ ID NO: 8.

In one embodiment, the second antigen binding moiety comprises a heavy chain variable region sequence that is at least about 95%, 96%, 97%, 98%, 99% or 100% identical to the amino acid sequence of SEQ ID NO: 15 and a light chain variable region sequence that is at least about 95%, 96%, 97%, 98%, 99% or 100% identical to the amino acid sequence of SEQ ID NO: 16.

In one embodiment, the second antigen binding moiety comprises the heavy chain variable region sequence of SEQ ID NO: 15 and the light chain variable region sequence of SEQ ID NO: 16.

In some embodiments, the first and/or the second antigen binding moiety is a Fab molecule. In some embodiments, the first antigen binding moiety is a crossover Fab molecule wherein either the variable or the constant regions of the Fab light chain and the Fab heavy chain are exchanged. In such embodiments, the second antigen binding moiety preferably is a conventional Fab molecule.

In some embodiments, the first and the second antigen binding moiety are fused to each other, optionally via a peptide linker.

In some embodiments, the first and the second antigen binding moiety are each a Fab molecule and either (i) the second antigen binding moiety is fused at the C-terminus of the Fab heavy chain to the N-terminus of the Fab heavy chain of the first antigen binding moiety, or (ii) the first antigen binding moiety is fused at the C-terminus of the Fab heavy chain to the N-terminus of the Fab heavy chain of the second antigen binding moiety.

In some embodiments, the CEA CD3 bispecific antibody provides monovalent binding to CD3.

In particular embodiments, the CEA CD3 bispecific antibody comprises a single antigen binding moiety that specifically binds to CD3, and two antigen binding moieties that specifically bind to CEA. Thus, in some embodiments, the CEA CD3 bispecific antibody comprises a third antigen binding moiety that specifically binds to CEA. In some embodiments, the third antigen moiety is identical to the first antigen binding moiety (e.g. is also a Fab molecule and comprises the same amino acid sequences).

In particular embodiments, the CEA CD3 bispecific antibody further comprises an Fc domain composed of a first and a second subunit. In one embodiment, the Fc domain is an IgG Fc domain. In a particular embodiment, the Fc domain is an $IgG_1$ Fc domain. In another embodiment the Fc domain is an IgG4 Fc domain. In a more specific embodiment, the Fc domain is an IgG4 Fc domain comprising an amino acid substitution at position S228 (Kabat EU index numbering), particularly the amino acid substitution S228P. This amino acid substitution reduces in vivo Fab arm exchange of $IgG_4$ antibodies (see Stubenrauch et al., Drug Metabolism and Disposition 38, 84-91 (2010)). In a further particular embodiment, the Fc domain is a human Fc domain. In a particularly preferred embodiment, the Fc domain is a human $IgG_1$ Fc domain. An exemplary sequence of a human $IgG_1$ Fc region is given in SEQ ID NO: 21.

In some embodiments wherein the first, the second and, where present, the third antigen binding moiety are each a Fab molecule, (a) either (i) the second antigen binding moiety is fused at the C-terminus of the Fab heavy chain to the N-terminus of the Fab heavy chain of the first antigen binding moiety and the first antigen binding moiety is fused at the C-terminus of the Fab heavy chain to the N-terminus of the first subunit of the Fc domain, or (ii) the first antigen binding moiety is fused at the C-terminus of the Fab heavy chain to the N-terminus of the Fab heavy chain of the second antigen binding moiety and the second antigen binding moiety is fused at the C-terminus of the Fab heavy chain to the N-terminus of the first subunit of the Fc domain; and (b) the third antigen binding moiety, where present, is fused at the C-terminus of the Fab heavy chain to the N-terminus of the second subunit of the Fc domain.

In particular embodiments, the Fc domain comprises a modification promoting the association of the first and the second subunit of the Fc domain. The site of most extensive protein-protein interaction between the two subunits of a human IgG Fc domain is in the CH3 domain. Thus, in one embodiment said modification is in the CH3 domain of the Fc domain.

In a specific embodiment said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain. The knob-into-hole technology is described e.g. in U.S. 5,731,168; U.S. Pat. No. 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in some embodiments, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable. Preferably said amino acid residue having a larger side chain volume is selected from the group consisting of arginine (R), phenylalanine (F), tyrosine (Y), and tryptophan (W). Preferably said amino acid residue having a smaller side chain volume is selected from the group consisting of alanine (A), serine (S), threonine (T), and valine (V). The protuberance and cavity can be made by altering the nucleic acid encoding the polypeptides, e.g. by site-specific mutagenesis, or by peptide synthesis.

In a specific such embodiment, in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numbering according to Kabat EU index). In a further embodiment, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numbering according to Kabat EU index). In a preferred embodiment, the first subunit of the Fc domain comprises the amino acid substitutions S354C and T366W, and the second subunit of the Fc domain comprises the amino acid substitutions Y349C, T366S, L368A and Y407V (numbering according to Kabat EU index).

In some embodiments, the Fc domain comprises one or more amino acid substitution that reduces binding to an Fc receptor and/or effector function.

In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of complement dependent cytotoxicity (CDC), antibody-dependent cell-mediated cytotoxicity (ADCC), antibody-dependent cellular phagocytosis (ADCP), and cytokine secretion. In a particular embodiment, the effector function is ADCC.

Typically, the same one or more amino acid substitution is present in each of the two subunits of the Fc domain. In one embodiment, the one or more amino acid substitution reduces the binding affinity of the Fc domain to an Fc receptor. In one embodiment, the one or more amino acid substitution reduces the binding affinity of the Fc domain to an Fc receptor by at least 2-fold, at least 5-fold, or at least 10-fold.

In one embodiment, the Fc domain comprises an amino acid substitution at a position selected from the group of E233, L234, L235, N297, P331 and P329 (numberings according to Kabat EU index). In a more specific embodiment, the Fc domain comprises an amino acid substitution at a position selected from the group of L234, L235 and P329 (numberings according to Kabat EU index). In some embodiments, the Fc domain comprises the amino acid substitutions L234A and L235A (numberings according to Kabat EU index). In one such embodiment, the Fc domain is an IgG$_1$ Fc domain, particularly a human IgG$_1$ Fc domain. In one embodiment, the Fc domain comprises an amino acid substitution at position P329. In a more specific embodiment, the amino acid substitution is P329A or P329G, particularly P329G (numberings according to Kabat EU index). In one embodiment, the Fc domain comprises an amino acid substitution at position P329 and a further amino acid substitution at a position selected from E233, L234, L235, N297 and P331 (numberings according to Kabat EU index). In a more specific embodiment, the further amino acid substitution is E233P, L234A, L235A, L235E, N297A, N297D or P331S. In particular embodiments, the Fc domain comprises amino acid substitutions at positions P329, L234 and L235 (numberings according to Kabat EU index). In more particular embodiments, the Fc domain comprises the amino acid mutations L234A, L235A and P329G ("P329G LALA", "PGLALA" or "LALAPG"). Specifically, in preferred embodiments, each subunit of the Fc domain comprises the amino acid substitutions L234A, L235A and P329G (Kabat EU index numbering), i.e. in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index). In one such embodiment, the Fc domain is an IgG$_1$ Fc domain, particularly a human IgG$_1$ Fc domain.

In a preferred embodiment, the CEA CD3 bispecific antibody comprises (i) a first antigen binding moiety that specifically binds to CD3, comprising a heavy chain variable region comprising the heavy chain CDR (HCDR) 1 of SEQ ID NO: 1, the HCDR2 of SEQ ID NO: 2, and the HCDR3 of SEQ ID NO: 3; and a light chain variable region comprising the light chain CDR (LCDR) 1 of SEQ ID NO: 4, the LCDR2 of SEQ ID NO: 5 and the LCDR3 of SEQ ID NO: 6, wherein the first antigen binding moiety is a crossover Fab molecule wherein either the variable or the constant regions, particularly the constant regions, of the Fab light chain and the Fab heavy chain are exchanged;

(ii) a second and a third antigen binding moiety that specifically bind to CEA, comprising a heavy chain variable region comprising the heavy chain CDR (HCDR) 1 of SEQ ID NO: 9, the HCDR2 of SEQ ID NO: 10, and the HCDR3 of SEQ ID NO: 11; and a light chain variable region comprising the light chain CDR (LCDR) 1 of SEQ ID NO: 12, the LCDR2 of SEQ ID NO: 13 and the LCDR3 of SEQ ID NO: 14, wherein the second and third antigen binding moiety are each a Fab molecule, particularly a conventional Fab molecule;

(iii) an Fc domain composed of a first and a second subunit, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain.

In one embodiment, the first antigen binding moiety comprises a heavy chain variable region sequence that is at least about 95%, 96%, 97%, 98%, 99% or 100% identical to the amino acid sequence of SEQ ID NO: 7 and a light chain variable region sequence that is at least about 95%, 96%, 97%, 98%, 99% or 100% identical to the amino acid sequence of SEQ ID NO: 8.

In one embodiment, the first antigen binding moiety comprises the heavy chain variable region sequence of SEQ ID NO: 7 and the light chain variable region sequence of SEQ ID NO: 8.

In one embodiment, the second and third antigen binding moiety comprise a heavy chain variable region sequence that is at least about 95%, 96%, 97%, 98%, 99% or 100% identical to the amino acid sequence of SEQ ID NO: 15 and a light chain variable region sequence that is at least about 95%, 96%, 97%, 98%, 99% or 100% identical to the amino acid sequence of SEQ ID NO: 16.

In one embodiment, the second and third antigen binding moieties comprise the heavy chain variable region of SEQ ID NO: 15 and the light chain variable region of SEQ ID NO: 16.

The Fc domain according to the above embodiments may incorporate, singly or in combination, all of the features described hereinabove in relation to Fc domains.

In one embodiment, the antigen binding moieties and the Fc region are fused to each other by peptide linkers, particularly by peptide linkers as in SEQ ID NO: 19 and SEQ ID NO: 20. In one embodiment, the CEA CD3 bispecific antibody comprises a polypeptide (particularly two polypeptides) comprising a sequence that is at least 80%, 85%, 90%, 95%, 96%, 97%, 98%, or 99% identical to the sequence of SEQ ID NO: 17, a polypeptide comprising a sequence that is at least 80%, 85%, 90%, 95%, 96%, 97%, 98%, or 99% identical to the sequence of SEQ ID NO: 18, a polypeptide comprising a sequence that is at least 80%, 85%, 90%, 95%, 96%, 97%, 98%, or 99% identical to the sequence of SEQ ID NO: 19, and a polypeptide comprising a sequence that is at least 80%, 85%, 90%, 95%, 96%, 97%, 98%, or 99% identical to the sequence of SEQ ID NO: 20.

In a particularly preferred embodiment, the CEA CD3 bispecific antibody comprises a polypeptide (particularly two polypeptides) comprising the sequence of SEQ ID NO: 17, a polypeptide comprising the sequence of SEQ ID NO: 18, a polypeptide comprising the sequence of SEQ ID NO: 19, and a polypeptide comprising the sequence of SEQ ID NO: 20. (CEA TCB)

In a particularly preferred embodiment, the CEA CD3 bispecific antibody is CEA TCB.

For the formulation according to the present invention the CEA CD3 bispecific antibody is used at a concentration of about 1 to about 200 mg/ml, preferably about 1 to about 100 mg/ml, more preferably about 10 to about 75 mg/ml, and most preferably about 20 to about 50 mg/ml. In a preferred embodiment, the formulation comprises about 20 to about 50 mg/ml CEA CD3 bispecific antibody, particularly about 50 mg/ml CEA CD3 bispecific antibody. In some embodiments, the formulation comprises about 5 mg/ml CEA CD3 bispecific antibody.

In a first aspect, the invention relates to a pharmaceutical formulation comprising:
  1 to 200 mg/ml of a CEA CD3 bispecific antibody;
  1 to 100 mM of a buffering agent;
  0.001 to 1% (w/v) of a surfactant;
  1 to 500 mM of at least one stabilizer;
  at a pH in the range of from 4.0 to 7.0.

Preferred CEA CD3 bispecific antibodies that may be comprised in the formulation according to the present invention are described in detail hereinabove. Particularly preferred is CEA TCB.

In a preferred embodiment, the concentration of the CEA CD3 bispecific antibody comprised in the formulation according to the invention is in the range of 1 to 100 mg/ml, preferably 10 to 75 mg/ml, most preferably 20 to 50 mg/ml. Particularly preferred is a concentration of 20 mg/ml or 50 mg/ml, most preferably 50 mg/ml. In a further preferred embodiment, the concentration of the CEA CD3 bispecific antibody is in the range of 5 to 50 mg/ml. Particularly preferred according to such embodiment is a concentration of 5 mg/ml, 20 mg/ml or 50 mg/ml. In a further preferred embodiment, the concentration of the CEA CD3 bispecific antibody is in the range of 1 to 10 mg/ml. Particularly preferred according to such embodiment is a concentration of 5 mg/ml.

In another preferred embodiment, the buffering agent comprised in the formulation according to the invention is a histidine buffer, preferably a L-histidine/HCl buffer. Particularly preferred is a L-histidine/HCl buffer (i.e. L-histidine as the buffering agent).

Preferably, the buffering agent is at a concentration of 10 to 50 mM, more preferably 15 to 30 mM, most preferably 20 mM.

Preferably, the buffering agent provides a pH of 5.0 to 6.0, more preferably 5.5±0.5, most preferably 5.5±0.3.

In a preferred embodiment, the surfactant comprised in the formulation according to the invention is a polysorbate, preferably polysorbate 20 or polysorbate 80, most preferably polysorbate 20.

Preferably, the surfactant is at a concentration of 0.01 to 0.1% (w/v), more preferably 0.02 to 0.05%, most preferably 0.05%.

In yet another preferred embodiment, the at least one stabilizer comprised in the formulation according to the invention is selected from the group of salts, preferably sodium chloride, saccharides, preferably trehalose dihydrate or sucrose, and amino acids, preferably arginine hydrochloride. Preferably the at least one stabilizer is sucrose.

Preferably, the at least one stabilizer is at a concentration of 120 to 300 mM, more preferably 220 to 250 mM, most preferably 230 to 240 mM.

In a preferred embodiment, the formulation according to the invention comprises a first stabilizer selected from the group of salts, saccharides and amino acids, and methionine as a second stabilizer.

In a preferred embodiment, the first stabilizer is at a concentration of 120 to 300 mM, preferably 220 to 250 mM, more preferably 230 to 240 mM, and the second stabilizer methionine is present at a concentration of 5 to 25 mM, preferably 5 to 15 mM, more preferably 10 mM.

In a particularly preferred embodiment, the formulation according to the invention comprises a saccharide, preferably sucrose, as a first stabilizer, and methionine as a second stabilizer. The saccharide is preferably at a concentration of about 230 mM (particularly in embodiments wherein the concentration of the CEA CD3 bispecific antibody is 50 mg/ml or more), and methionine is preferably at a concentration of about 10 mM. In some embodiments, particularly in embodiments wherein the concentration of the CEA CD3 bispecific antibody is below 50 mg/ml (e.g. 5 mg/ml, or 20 mg/ml), the saccharide is at a concentration of about 240 mM and methionine is at a concentration of about 10 mM.

In one embodiment, the formulation according to the invention comprises:
  5 to 50 mg/ml of a CEA CD3 bispecific antibody;
  15 to 30 mM L-histidine;
  0.02 to 0.05% (w/v) polysorbate 20;
  120 to 300 mM sucrose;
  optionally, 5 to 25 mM methionine;
  at a pH of 5.5±0.5.

In a further embodiment, the formulation according to the invention comprises:
  5 to 50 mg/ml of a CEA CD3 bispecific antibody;
  15 to 25 mM L-histidine;
  0.03 to 0.05% (w/v) polysorbate 20;
  220 to 250 mM sucrose;

5 to 15 mM methionine;
at a pH of 5.5±0.5.

In a further embodiment, the formulation according to the invention comprises:
5 to 50 mg/ml of a CEA CD3 bispecific antibody;
15 to 25 mM L-histidine;
0.03 to 0.05% (w/v) polysorbate 20;
220 to 250 mM sucrose;
5 to 15 mM methionine;
at a pH of 5.5±0.3.

In still a further embodiment, the formulation according to the invention comprises:
20 to 50 mg/ml of a CEA CD3 bispecific antibody;
15 to 30 mM L-histidine;
0.02 to 0.05% (w/v) polysorbate 20;
120 to 300 mM sucrose;
optionally, 5 to 25 mM methionine;
at a pH of 5.5±0.5.

In a further embodiment, the formulation according to the invention comprises:
20 to 50 mg/ml of a CEA CD3 bispecific antibody;
15 to 25 mM L-histidine;
0.03 to 0.05% (w/v) polysorbate 20;
220 to 250 mM sucrose;
5 to 15 mM methionine;
at a pH of 5.5±0.5.

In a further embodiment, the formulation according to the invention comprises:
20 to 50 mg/ml of a CEA CD3 bispecific antibody;
15 to 25 mM L-histidine;
0.03 to 0.05% (w/v) polysorbate 20;
220 to 250 mM sucrose;
5 to 15 mM methionine;
at a pH of 5.5±0.3.

In still a further embodiment, the formulation according to the invention comprises:
1 to 10 mg/ml of a CEA CD3 bispecific antibody;
15 to 30 mM L-histidine;
0.02 to 0.05% (w/v) polysorbate 20;
120 to 300 mM sucrose;
optionally, 5 to 25 mM methionine;
at a pH of 5.5±0.5.

In a further embodiment, the formulation according to the invention comprises:
1 to 10 mg/ml of a CEA CD3 bispecific antibody;
15 to 25 mM L-histidine;
0.03 to 0.05% (w/v) polysorbate 20;
220 to 250 mM sucrose;
5 to 15 mM methionine;
at a pH of 5.5±0.5.

In a further embodiment, the formulation according to the invention comprises:
1 to 10 mg/ml of a CEA CD3 bispecific antibody;
15 to 25 mM L-histidine;
0.03 to 0.05% (w/v) polysorbate 20;
220 to 250 mM sucrose;
5 to 15 mM methionine;
at a pH of 5.5±0.3.

In a particularly preferred embodiment, the formulation according to the invention comprises:
50 mg/ml of a CEA CD3 bispecific antibody, preferably CEA TCB;
20 mM L-histidine;
0.05% (w/v) polysorbate 20;
230 mM sucrose;
10 mM methionine;
at a pH of 5.5±0.5.

In a further preferred embodiment, the formulation according to the invention comprises:
50 mg/ml of a CEA CD3 bispecific antibody, preferably CEA TCB;
20 mM L-histidine;
0.05% (w/v) polysorbate 20;
230 mM sucrose;
10 mM methionine;
at a pH of 5.5±0.3.

In a further preferred embodiment, the formulation according to the invention comprises:
20 mg/ml of a CEA CD3 bispecific antibody, preferably CEA TCB;
20 mM L-histidine;
0.05% (w/v) polysorbate 20;
240 mM sucrose;
10 mM methionine;
at a pH of 5.5±0.5.

In a further preferred embodiment, the formulation according to the invention comprises:
20 mg/ml of a CEA CD3 bispecific antibody, preferably CEA TCB;
20 mM L-histidine;
0.05% (w/v) polysorbate 20;
240 mM sucrose;
10 mM methionine;
at a pH of 5.5±0.3.

In a further preferred embodiment, the formulation according to the invention comprises:
5 mg/ml of a CEA CD3 bispecific antibody, preferably CEA TCB;
20 mM L-histidine;
0.05% (w/v) polysorbate 20;
240 mM sucrose;
10 mM methionine;
at a pH of 5.5±0.5.

In a further preferred embodiment, the formulation according to the invention comprises:
5 mg/ml of a CEA CD3 bispecific antibody, preferably CEA TCB;
20 mM L-histidine;
0.05% (w/v) polysorbate 20;
240 mM sucrose;
10 mM methionine;
at a pH of 5.5±0.3.

In certain embodiments, the formulation according to the invention does not comprise sodium chloride. In certain embodiments, the formulation does not comprise a divalent cation. In certain embodiments, the formulation does not comprise citrate. In certain embodiments, the formulation does not comprise a polyol. In certain embodiments, the formulation does not comprise a dextran. In certain embodiments, the formulation does not comprise lysine.

The formulation according to the invention can be in a liquid form, in a lyophilized form or in a liquid form reconstituted from a lyophilized form. In certain embodiments, the formulation is in a liquid form.

The term "liquid" as used herein in connection with the formulation according to the invention denotes a formulation which is liquid at a temperature of at least about 2 to about 8° C. under atmospheric pressure.

The term "lyophilized" as used herein in connection with the formulation according to the invention denotes a formulation which is manufactured by freeze-drying methods known in the art per se. The solvent (e.g. water) is removed by freezing followed by sublimation of the ice under vacuum and desorption of residual water at elevated temperature. The lyophilizate usually has a residual moisture of about 0.1 to 5% (w/w) and is present as a powder or a physically stable cake. The lyophilizate is characterized by a fast dissolution after addition of a reconstitution medium.

The term "reconstituted form" as used herein in connection with the formulation according to the invention denotes a formulation which is lyophilized and re-dissolved by addition of reconstitution medium. Suitable reconstitution media comprise but are not limited to water for injection (WFI), bacteriostatic water for injection (BWFI), sodium chloride solutions (e.g. 0.9% (w/v) NaCl), glucose solutions (e.g. 5% glucose), surfactant-containing solutions (e.g. 0.01% polysorbate 20), pH-buffered solutions (e.g. phosphate-buffered solutions).

The formulation according to the invention is physiologically well tolerated, can be prepared easily, can be dispensed precisely and is stable with respect to decomposition products and aggregates over the duration of storage, during repeated freezing and thawing cycles and mechanical stress.

The invention further comprises a process for the preparation of the formulations according to the invention. Said process comprises buffer-exchanging the CEA CD3 bispecific antibody against a diafiltration buffer containing the anticipated buffer composition, and, where required, concentration of the antibody by diafiltration, followed by adding the excipients (e.g. trehalose dihydrate, sucrose, arginine, sodium chloride, methionine) as stock solutions to the antibody solution, followed by adding the surfactant as stock solution to the antibody/excipient solution, and finally adjusting the antibody concentration to the desired final concentration using buffer solution, whereby also the final excipient and surfactant concentrations are reached.

Alternatively, the excipients can also be added as solids to the starting solution comprising the CEA CD3 bispecific antibody. If the CEA CD3 bispecific antibody is in the form of a solid, e.g. a lyophilizate, the formulation according to the invention can be prepared by firstly dissolving the bispecific antibody in water or buffer solution, optionally comprising one or more of the excipients, and subsequently adding the further excipients as stock solutions or solids. The CEA CD3 bispecific antibody can advantageously also be dissolved directly in a solution comprising all further excipients. One or more of the excipients present in the formulation according to the invention may already be added during or at the end of the process for the preparation of the CEA CD3 bispecific antibody, e.g. by dissolving the CEA CD3 bispecific antibody directly in a solution comprising one, more than one, or preferably all of the excipients of the formulation in the final step of the purification carried out after the preparation of the bispecific antibody. If the solution comprising the bispecific antibody and the excipients does not yet have the desired pH, this is adjusted by addition of an acid or base, preferably using the acid or base already present in the buffer system. This is followed by sterile filtration.

The invention further comprises the formulations according to the invention for use in treating diseases, or the use of the formulations according to the invention for the preparation of a medicament useful for treating diseases, particularly cell proliferation disorders, wherein CEA is expressed, particularly wherein CEA is abnormally expressed (e.g., overexpressed) compared to normal tissue of the same cell type. Such disorders include different types of cancer, such as colorectal cancer, lung cancer, pancreatic cancer, breast cancer, and gastric cancer. CEA expression levels may be determined by methods known in the art (e.g., via immunohistochemistry assay, immunofluorescence assay, immunoenzyme assay, ELISA, flow cytometry, radioimmunoassay, Western blot, ligand binding, kinase activity, etc.). The invention also comprises methods for treating diseases as described hereinabove, comprising administering a formulation according to the invention to an individual in need thereof.

A formulation of the present invention can be administered by a variety of methods known in the art. As will be appreciated by the skilled artisan, the route and/or mode of administration will vary depending upon the desired results.

To administer a formulation of the invention by certain routes of administration, it may be necessary to dilute the formulation in a diluent. Pharmaceutically acceptable diluents include saline, glucose, Ringer and aqueous buffer solutions.

Preferably, the formulation according to the invention is administered by intravenous (i.v.), subcutaneous (s.c.), or any other parental administration means such as those known in the pharmaceutical art.

The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The formulation must be sterile and fluid to the extent that the formulation is deliverable by syringe or an infusion system. In addition to water, the carrier can be an isotonic buffered saline solution, ethanol, polyol (e.g., glycerol, propylene glycol, and liquid polyethylene glycol, and the like), and suitable mixtures thereof.

The formulation according to the invention can be prepared by methods known in the art, e.g. ultrafiltration-diafiltration, dialysis, addition and mixing, lyophilisation, reconstitution, and combinations thereof. Examples of preparations of formulations according to the invention can be found hereinafter.

The examples explain the invention in more detail but should not be construed as limiting the scope of the invention. The disclosures of all patent and scientific literature cited herein are expressly incorporated in their entirety by reference.

EXAMPLES

The CEA CD3 bispecific antibody formulations according to the invention were developed based on the experimental results as provided below using the general preparatory and analytical methods and assays as outlined below.

Example 1

Preparation of the Components for the Formulation

The CEA CD3 bispecific antibody CEA TCB was manufactured by techniques generally known from the production of recombinant proteins. For preparing the formulations in accordance with these examples the CEA TCB antibody was provided at a concentration approx. 20-30% above target concentration in a 20 mM histidine buffer (a L-histidine/HCl buffer) at a pH of approximately 5.5.

The excipients of the formulation in accordance with the present invention are widely used in the practice and known to the person skilled in the art. There is therefore no need to explain them here in detail.

Liquid drug product formulations according to the invention were developed as follows.

Example 2

Preparation of the Liquid Formulations

For the preparation of the liquid formulations CEA TCB was buffer-exchanged against a diafiltration buffer containing the anticipated buffer composition and where required, concentrated by diafiltration to an antibody concentration approx. 20-30% above target concentration. After completion of the diafiltration operation, the excipients (e.g. sucrose, sodium chloride, methionine) were added as stock solutions to the antibody solution. The surfactant was then added as a 50 to 200-fold stock solution. Finally, the protein concentration was adjusted with a buffer to the final CEA TCB concentration of approx. 5 mg/ml or approx. 20 mg/ml or approx. 50 mg/ml.

All formulations were sterile-filtered through 0.22 μm low protein binding filters and aseptically filled into sterile 6 ml glass vials closed with ETFE (copolymer of ethylene and tetrafluoroethylene)-coated rubber stoppers and aluminum crimp caps. The fill volume was approx. 2.7 ml. These formulations were stored at different ICH climate conditions (5° C., 25° C. and 40° C.) for different intervals of time and stressed by shaking (1 week at a shaking frequency of 200 min' at 5° C. and 25° C.) and freeze-thaw stress methods. The samples were analyzed before and after applying the stress tests by the following analytical methods:

1) UV spectrophotometry;
2) Size Exclusion Chromatography (SEC);
3) Ion Exchange Chromatography (IEC);
4) measurement of the turbidity of the solution;
5) inspection for visible particles.

UV spectroscopy, used for determination of protein content, was performed on a Perkin Elmer λ35 UV spectrophotometer in a wavelength range from 240 nm to 400 nm. Neat protein samples were diluted to approx. 0.5 mg/ml with the corresponding formulation buffer. The protein concentration was calculated according to Equation 1.

$$\text{Protein content} = \frac{(A_{280nm} - A_{320nm}) \times dil.factor}{\varepsilon \left[\frac{cm^2}{mg}\right] \times d_{cm}} \quad \text{Equation 1}$$

The UV light absorption at 280 nm was corrected for light scattering at 320 nm and multiplied with the dilution factor, which was determined from the weighed masses and densities of the neat sample and the dilution buffer. The numerator was divided by the product of the cuvette's path length d and the extinction coefficient ε.

Size Exclusion Chromatography (SEC) was used to detect soluble high molecular weight species (aggregates) and low molecular weight hydrolysis products (LMW) in the formulations. The method was performed on a Waters Alliance HPLC instrument with a UV Detector and equipped with a Tosoh Bioscience TSK-Gel G3000SWXL column. Intact monomer, aggregates and hydrolysis products were separated by an isocratic elution profile, using 0.2 M potassium phosphate, 0.25 M potassium chloride, pH 7.0 as mobile phase, and were detected at a wavelength of 280 nm.

Ion Exchange Chromatography (IEC) was performed to detect chemical degradation products altering the net charge of CEA TCB in the formulations. The method used a suitable HPLC instrument equipped with a UV detector (detection wavelength 280 nm) and a ThermoScientific MabPac SCX-10 BioLC column (4 mm×250 mm). 10 mM HEPES, pH 7.7 in water and 10 mM HEPES, 1 M NaCl, pH 7.7 were used as mobile phases A and B, respectively, with a flow rate of 1.0 mL/min.

For the determination of the turbidity, opalescence was measured in FTU (turbidity units) using a HACH 2100AN turbidimeter at room temperature.

Samples of Formulations A, B, C, H, I and J were analyzed for visible particles by using a Seidenader V90-T visual inspection instrument. Samples of Formulation D, E, F and G were analyzed for visible particles using a Simplex Ampoule Testing Apparatus OPTIMA I.

The results of the stability testing for the Formulations A to J are provided in Table 1 added below.

The results show that for obtaining maximum antibody stability and antibody formulations free from particles, L-histidine/HCl buffer is the most favorable buffer, sucrose in combination with methionine are the most favorable stabilizers, and polysorbate 20 is the most favorable surfactant.

TABLE 1

Composition and stability data of liquid CEA CD3 bispecific antibody formulations according to this invention

| Storage condition | Storage Time | Protein concentration (mg/ml) | Size Exclusion-HPLC | | | Ion Exchange-HPLC | | | Turbidity (FTU) | Visible particles (per container) |
|---|---|---|---|---|---|---|---|---|---|---|
| | | | HMW (%) | Main peak (%) | LMW (%) | Acidic Peak (%) | Main Peak (%) | Basic Peak (%) | | |
| Formulation A is a liquid formulation with the composition 50 mg/ml CEA TCB, 20 mM L-histidine pH 5.5, 230 mM sucrose, 0.05% polysorbate 20, 10 mM methionine. | | | | | | | | | | |
| — | Initial | 49.5 | 1.6 | 98.2 | 0.1 | 25.5 | 71.9 | 2.6 | 7.0 | 0 |
| Shaking 5° C. | 1 week | n/a | 1.6 | 98.2 | 0.2 | 25.2 | 71.8 | 3 | 7.0 | 0 |
| Shaking 25° C. | 1 week | n/a | 1.6 | 98.2 | 0.2 | 25.4 | 71.8 | 2.8 | 7.1 | 0 |
| Freezing/Thawing | (5 cycles) | n/a | 1.6 | 98.2 | 0.2 | 25.5 | 72.1 | 2.4 | 7.0 | 0 |
| 2-8° C. | 5 weeks | n/a | 1.6 | 98.2 | 0.2 | 25.3 | 71.9 | 2.8 | 7.6 | 0 |
| | 8 weeks | 49.4 | 1.6 | 98.2 | 0.2 | 25.0 | 72.3 | 2.7 | 7.3 | 0 |
| | 12 weeks | 49.2 | 1.7 | 98.1 | 0.2 | 25.2 | 72.3 | 2.5 | 7.7 | 0 |
| | 24 weeks | 49.7 | 1.7 | 98.0 | 0.3 | 25.0 | 71.6 | 3.5 | 7.5 | 0 |
| | 36 weeks | n/a | 1.7 | 98.0 | 0.4 | 26.3 | 71.0 | 2.6 | 7.2 | 0 |

TABLE 1-continued

Composition and stability data of liquid CEA CD3 bispecific antibody formulations according to this invention

| Storage condition | Storage Time | Protein concentration (mg/ml) | Size Exclusion-HPLC | | | Ion Exchange-HPLC | | | Turbidity (FTU) | Visible particles (per container) |
|---|---|---|---|---|---|---|---|---|---|---|
| | | | HMW (%) | Main peak (%) | LMW (%) | Acidic Peak (%) | Main Peak (%) | Basic Peak (%) | | |
| 25° C. | 5 weeks | n/a | 1.6 | 97.9 | 0.5 | 26.3 | 70.8 | 2.9 | 7.5 | 0 |
| | 8 weeks | 50 | 1.6 | 97.7 | 0.6 | 26.9 | 70.4 | 2.8 | 7.8 | 0 |
| | 12 weeks | 50.2 | 1.7 | 97.5 | 0.8 | 28.7 | 68.4 | 2.9 | 7.8 | 0 |
| | 24 weeks | 49.9 | 1.7 | 97.0 | 1.3 | 31.4 | 64.7 | 3.9 | 7.5 | 0 |
| 40° C. | 5 weeks | n/a | 2.0 | 95.7 | 2.3 | 37.3 | 59 | 3.7 | 9.7 | 0 |
| | 8 weeks | 50 | 1.6 | 94.6 | 3.8 | 44.9 | 51.2 | 3.9 | 10.1 | 0 |
| | 12 weeks | 50 | 3 | 92.1 | 5.0 | 52.6 | 43.3 | 4.1 | 11.0 | 0 |
| Formulation B is a liquid formulation with the composition 50 mg/ml CEA TCB, 20 mM L-histidine pH 5.5, 130 mM sodium chloride, 0.05% polysorbate 20. | | | | | | | | | | |
| — | Initial | 49.6 | 1.8 | 98.1 | 0.1 | 25.4 | 71.8 | 2.8 | 28.3 | 0 |
| Shaking 5° C. | 1 week | n/a | 1.8 | 98 | 0.2 | 25.3 | 71.8 | 3 | 28.6 | 0 |
| Shaking 25° C. | 1 week | n/a | 1.9 | 97.9 | 0.2 | 25.1 | 71.8 | 3.1 | 28.5 | 0 |
| Freezing/ Thawing | (5 cycles) | n/a | 1.7 | 98.1 | 0.2 | 25.4 | 72 | 2.6 | 28.6 | 0 |
| 2-8° C. | 5 weeks | n/a | 1.9 | 97.9 | 0.2 | 25 | 72 | 3 | 30.4 | 0 |
| | 8 weeks | 50 | 1.9 | 97.9 | 0.2 | 24.7 | 72.4 | 2.9 | 29.4 | 0 |
| | 12 weeks | 49.3 | 2.1 | 97.7 | 0.2 | 25.1 | 72.2 | 2.7 | 30.0 | 0 |
| 25° C. | 5 weeks | n/a | 2.1 | 97.4 | 0.5 | 25.7 | 70.7 | 3.6 | 29.5 | 0 |
| | 8 weeks | 49.7 | 2.2 | 97.1 | 0.7 | 25.8 | 70.8 | 3.4 | 30.2 | 0 |
| | 12 weeks | 49.7 | 2.4 | 96.7 | 0.9 | 27.5 | 69.2 | 3.3 | 30.1 | >10 |
| 40° C. | 5 weeks | n/a | 3.3 | 94.0 | 2.7 | 34.4 | 60.8 | 4.8 | 44.8 | >10 |
| | 8 weeks | 48.8 | 2.4 | 93.4 | 4.2 | 39.8 | 55.6 | 4.7 | 56.4 | >10 |
| | 12 weeks | 48.9 | 4.7 | 89.3 | 5.9 | 47.1 | 47.9 | 5.0 | 59.4 | >10 |
| Formulation C is a liquid formulation with the composition 50 mg/ml CEA TCB, 20 mM L-histidine pH 5.5, 230 mM sucrose, 0.05% polysorbate 20. | | | | | | | | | | |
| — | Initial | 49.4 | 1.7 | 98.2 | 0.1 | 25.5 | 72.0 | 2.6 | 7.2 | 0 |
| Shaking 5° C. | 1 week | n/a | 1.7 | 98.2 | 0.2 | 25.1 | 71.9 | 3 | 7.0 | 0 |
| Shaking 25° C. | 1 week | n/a | 1.6 | 98.1 | 0.2 | 25.4 | 71.7 | 2.9 | 7.1 | 0 |
| Freezing/ Thawing | (5 cycles) | n/a | 1.6 | 98.2 | 0.2 | 25.4 | 72.2 | 2.4 | 7.1 | 0 |
| 2-8° C. | 5 weeks | n/a | 1.7 | 98.1 | 0.2 | 25.3 | 71.9 | 2.8 | 7.8 | 0 |
| | 8 weeks | 49.2 | 1.6 | 98.1 | 0.2 | 25.0 | 72.3 | 2.7 | 7.4 | 0 |
| | 12 weeks | 49.1 | 1.8 | 98.0 | 0.3 | 25.3 | 72.2 | 2.5 | 7.9 | 0 |
| 25° C. | 5 weeks | n/a | 1.7 | 97.8 | 0.5 | 26.3 | 70.7 | 3 | 7.7 | 0 |
| | 8 weeks | 50.1 | 1.7 | 97.6 | 0.7 | 26.7 | 70.4 | 2.9 | 7.8 | 0 |
| | 12 weeks | 49.6 | 1.9 | 97.3 | 0.8 | 28.5 | 68.6 | 2.9 | 8.0 | 0 |
| 40° C. | 5 weeks | n/a | 2.2 | 95.4 | 2.4 | 37.6 | 58.5 | 3.8 | 9.4 | 0 |
| | 8 weeks | 50 | 2 | 94.1 | 3.9 | 45.6 | 50.5 | 3.9 | 10.6 | 0 |
| | 12 weeks | 49.9 | 4 | 91.0 | 5.0 | 53.2 | 42.5 | 4.3 | 11.2 | 0 |
| Formulation D is a liquid formulation with the composition 5 mg/ml CEA TCB, 20 mM L-histidine pH 5.5, 240 mM sucrose, 10 mM Methionine, 0.05% polysorbate 20. | | | | | | | | | | |
| — | Initial | 4.9 | 1.0 | 98.9 | 0.0 | 30.3 | 66.6 | 3.1 | 2.1 | 2 |
| Shaking 5° C. | 1 week | 4.9 | 1.0 | 98.9 | 0.1 | 30.6 | 66.2 | 3.2 | 2.2 | 0 |
| Shaking 25° C. | 1 week | 4.9 | 1.0 | 98.8 | 0.2 | 30.4 | 66.1 | 3.5 | 2.2 | 0 |
| Freezing/ Thawing | (5 cycles) | 4.9 | 1.0 | 98.9 | 0.1 | 30.5 | 66.5 | 3.0 | 2.3 | 0 |
| 2-8° C. | 4 weeks | 4.9 | 1.0 | 98.8 | 0.2 | 30.6 | 66.3 | 3.1 | 2.2 | 0 |
| | 8 weeks | 5.0 | 1.0 | 98.8 | 0.1 | 30.5 | 66.3 | 3.1 | 2.2 | 0 |
| | 13 weeks | 4.8 | 0.9 | 98.8 | 0.3 | 30.8 | 66.3 | 2.9 | 2.2 | 0 |
| 25° C. | 4 weeks | 4.9 | 1.0 | 98.7 | 0.3 | 30.5 | 65.7 | 3.9 | 2.2 | 0 |
| | 8 weeks | 4.8 | 1.0 | 98.6 | 0.4 | 31.4 | 64.9 | 3.8 | 2.3 | 0 |
| | 13 weeks | 4.8 | 0.9 | 98.5 | 0.7 | 32.8 | 63.7 | 3.5 | 2.1 | 0 |
| 40° C. | 4 weeks | 4.9 | 1.0 | 97.4 | 1.6 | 37.8 | 57.1 | 5.1 | 2.2 | 0 |
| | 8 weeks | 4.9 | 1.2 | 95.8 | 3.0 | 39.0 | 56.2 | 4.8 | 2.2 | 0 |
| | 13 weeks | 4.9 | 1.2 | 94.1 | 4.7 | 68.5 | 27.2 | 4.3 | 2.4 | 0 |
| Formulation E is a liquid formulation with the composition 5 mg/ml CEA TCB, 20 mM L-histidine pH 5.5, 240 mM sucrose, 0.05% polysorbate 20. | | | | | | | | | | |
| — | Initial | 5.1 | 1.0 | 98.9 | 0.0 | 30.2 | 66.8 | 3.0 | 2.2 | 0 |
| Shaking 5° C. | 1 week | 5.1 | 1.1 | 98.9 | 0.0 | 30.6 | 66.4 | 3.0 | 2.4 | 0 |
| Shaking 25° C. | 1 week | 5.1 | 1.0 | 98.8 | 0.2 | 30.4 | 66.0 | 3.6 | 2.3 | 0 |
| Freezing/ Thawing | (5 cycles) | 5.1 | 1.0 | 98.8 | 0.1 | 30.6 | 66.3 | 3.1 | 2.3 | 0 |
| 2-8° C. | 4 weeks | 5.1 | 1.1 | 98.8 | 0.2 | 30.6 | 66.4 | 3.0 | 2.2 | 0 |
| | 8 weeks | 5.1 | 1.1 | 98.8 | 0.2 | 30.5 | 66.4 | 3.1 | 2.4 | 0 |
| 25° C. | 4 weeks | 5.1 | 1.0 | 98.7 | 0.3 | 30.7 | 98.7 | 3.9 | 2.4 | 0 |

TABLE 1-continued

Composition and stability data of liquid CEA CD3 bispecific antibody formulations according to this invention

| Storage condition | Storage Time | Protein concentration (mg/ml) | Size Exclusion-HPLC HMW (%) | Main peak (%) | LMW (%) | Ion Exchange-HPLC Acidic Peak (%) | Main Peak (%) | Basic Peak (%) | Turbidity (FTU) | Visible particles (per container) |
|---|---|---|---|---|---|---|---|---|---|---|
|  | 8 weeks | 5.0 | 1.0 | 98.5 | 0.5 | 31.9 | 98.5 | 3.9 | 2.3 | 0 |
| 40° C. | 4 weeks | 5.1 | 2.0 | 95.7 | 2.2 | 34.8 | 59.5 | 5.7 | 2.3 | 0 |
|  | 8 weeks | 5.1 | 6.0 | 89.7 | 4.3 | 49.5 | 43.8 | 6.7 | 2.8 | 0 |
| | Formulation F is a liquid formulation with the composition 5 mg/ml CEA TCB, L-histidine pH 5.5. |

| Storage condition | Storage Time | Protein concentration (mg/ml) | HMW (%) | Main peak (%) | LMW (%) | Acidic Peak (%) | Main Peak (%) | Basic Peak (%) | Turbidity (FTU) | Visible particles (per container) |
|---|---|---|---|---|---|---|---|---|---|---|
| — | Initial | 4.6 | 1.6 | 98.2 | 0.1 | 18.4 | 81.6 | 0 | 2.5 | 0 |
| Shaking 5° C. | 1 week | n/a | n/a | n/a | n/a | n/a | n/a | n/a | n/a | n/a |
| Shaking 25° C. | 1 week | n/a | n/a | n/a | n/a | n/a | n/a | n/a | n/a | n/a |
| Freezing/Thawing | (5 cycles) | n/a | n/a | n/a | n/a | n/a | n/a | n/a | n/a | n/a |
| 2-8° C. | 4 weeks | 4.4 | 1.6 | 98.3 | 0.1 | 19.2 | 80.8 | 0 | 2.4 | 0 |
| 25° C. | 4 weeks | 4.5 | 1.6 | 98.1 | 0.3 | 19.7 | 80.3 | 0 | 2.5 | 0 |
| 40° C. | 4 weeks | 4.5 | 1.7 | 96.7 | 1.7 | 29.3 | 70.7 | 0 | 2.4 | 0 |

Formulation G is a liquid formulation with the composition 5 mg/ml CEA TCB, 20 mM Na—PO3 pH 7.0.

| Storage condition | Storage Time | Protein concentration (mg/ml) | HMW (%) | Main peak (%) | LMW (%) | Acidic Peak (%) | Main Peak (%) | Basic Peak (%) | Turbidity (FTU) | Visible particles (per container) |
|---|---|---|---|---|---|---|---|---|---|---|
| — | Initial | 5.0 | 2.1 | 97.7 | 0.1 | 19.3 | 80.7 | 0 | 3.6 | 0 |
| Shaking 5° C. | 1 week | n/a | n/a | n/a | n/a | n/a | n/a | n/a | n/a | n/a |
| Shaking 25° C. | 1 week | n/a | n/a | n/a | n/a | n/a | n/a | n/a | n/a | n/a |
| Freezing/Thawing | (5 cycles) | n/a | n/a | n/a | n/a | n/a | n/a | n/a | n/a | n/a |
| 2-8° C. | 4 weeks | 5.0 | 2.2 | 97.7 | 0.2 | 21.0 | 79.0 | 0 | 3.5 | 0 |
| 25° C. | 4 weeks | 5.0 | 2.5 | 97.1 | 0.3 | 37.6 | 62.4 | 0 | 3.9 | 0 |
| 40° C. | 4 weeks | 5.0 | 4.2 | 93.0 | 2.8 | 89.5 | 10.5 | 0 | 3.7 | >7 |

Formulation H is a liquid formulation with the composition 50 mg/ml CEA TCB, 20 mM L-histidine pH 5.5, 240 mM sucrose, 0.05% polysorbate 20.

| Storage condition | Storage Time | Protein concentration (mg/ml) | HMW (%) | Main peak (%) | LMW (%) | Acidic Peak (%) | Main Peak (%) | Basic Peak (%) | Turbidity (FTU) | Visible particles (per container) |
|---|---|---|---|---|---|---|---|---|---|---|
| — | Initial | 50.0 | 1.0 | 98.8 | 0.2 | 20.3 | 77.7 | 2.0 | 7.2 | 0 |
| Shaking 5° C. | 1 week | n/a | 1.0 | 98.7 | 0.3 | 20.00 | 77.8 | 2.1 | 7.1 | 0 |
| Shaking 25° C. | 1 week | n/a | 1.1 | 98.6 | 0.3 | 20.20 | 77.7 | 2 | 7.9 | 0 |
| Freezing/Thawing | (5 cycles) | n/a | 1.0 | 98.7 | 0.2 | 20.2 | 77.6 | 2.1 | 7.2 | 1-5 |
| 2-8° C. | 4 weeks | n/a | 0.9 | 98.8 | 0.3 | 20.1 | 77.8 | 2.1 | 7.3 | 0 |
|  | 7 weeks | n/a | 1.1 | 98.8 | 0.2 | 20.3 | 77.3 | 2.3 | 7.1 | 1-5 |
| 25° C. | 4 weeks | n/a | 1.1 | 98.4 | 0.5 | 21.7 | 76.2 | 2.1 | 8.4 | 0 |
|  | 7 weeks | 50.1 | 1.3 | 98.1 | 0.6 | 26.3 | 70.9 | 2.7 | 7.8 | 0 |
| 40° C. | 4 weeks | n/a | 1.6 | 95.9 | 2.5 | 35.4 | 61.5 | 3.1 | 8.9 | 0 |
|  | 7 weeks | 50.5 | 4.5 | 91.8 | 3.7 | 45.8 | 49.9 | 4.4 | 10.8 | 0 |

Formulation I is a liquid formulation with the composition 50 mg/ml CEA TCB, 20 mM L-histidine pH 5.5, 240 mM sucrose, 0.05% poloxamer 188.

| Storage condition | Storage Time | Protein concentration (mg/ml) | HMW (%) | Main peak (%) | LMW (%) | Acidic Peak (%) | Main Peak (%) | Basic Peak (%) | Turbidity (FTU) | Visible particles (per container) |
|---|---|---|---|---|---|---|---|---|---|---|
| — | Initial | 50.4 | 1.0 | 98.8 | 0.2 | 20.4 | 77.8 | 1.8 | 7.5 | 0 |
| Shaking 5° C. | 1 week | n/a | 1.0 | 98.7 | 0.2 | 20.20 | 78 | 1.8 | 7.8 | >10 |
| Shaking 25° C. | 1 week | n/a | 1.1 | 98.6 | 0.3 | 20.40 | 77.7 | 1.9 | 9.6 | >10 |
| Freezing/Thawing | (5 cycles) | n/a | 1.0 | 98.7 | 0.2 | 20.4 | 77.4 | 2.3 | 7.6 | 0 |
| 2-8° C. | 4 weeks | n/a | 0.9 | 98.8 | 0.3 | 20.2 | 77.8 | 2.0 | 7.6 | 0 |
|  | 7 weeks | n/a | 1.1 | 98.8 | 0.2 | 20.3 | 77.6 | 2.2 | 7.5 | 0 |
| 25° C. | 4 weeks | n/a | 1.1 | 98.4 | 0.5 | 24.0 | 73.9 | 2.1 | 9.1 | 0 |
|  | 7 weeks | 50.3 | 1.3 | 98.1 | 0.6 | 28.0 | 69.3 | 2.6 | 8.9 | >10 |
| 40° C. | 4 weeks | n/a | 1.6 | 95.9 | 2.5 | 35.4 | 61.4 | 3.2 | 9.1 | 0 |
|  | 7 weeks | 50.4 | 3.8 | 92.5 | 3.7 | 46.2 | 49.3 | 4.5 | 9.5 | 1-5 |

Formulation J is a liquid formulation with the composition 50 mg/ml CEA TCB, 20 mM L-histidine pH 5.5, 240 mM sucrose.

| Storage condition | Storage Time | Protein concentration (mg/ml) | HMW (%) | Main peak (%) | LMW (%) | Acidic Peak (%) | Main Peak (%) | Basic Peak (%) | Turbidity (FTU) | Visible particles (per container) |
|---|---|---|---|---|---|---|---|---|---|---|
| — | Initial | 49.7 | 1.0 | 98.8 | 0.2 | 20.3 | 77.6 | 2.0 | 7.0 | 0 |
| Shaking 5° C. | 1 week | n/a | 1.1 | 98.7 | 0.2 | 19.90 | 77.9 | 2.2 | 7.6 | >10 |
| Shaking 25° C. | 1 week | n/a | 3.0 | 96.7 | 0.3 | 19.80 | 77.6 | 2.6 | 95.5 | >10 |
| Freezing/Thawing | (5 cycles) | n/a | 1.0 | 98.7 | 0.2 | 20.2 | 77.9 | 1.9 | 7.3 | >10 |
| 2-8° C. | 4 weeks | n/a | 0.9 | 98.8 | 0.3 | 20.0 | 77.9 | 2.1 | 6.9 | 0 |
|  | 7 weeks | n/a | 1.0 | 98.8 | 0.2 | 20.3 | 77.3 | 2.4 | 7.2 | >10 |
| 25° C. | 4 weeks | n/a | 1.0 | 98.5 | 0.5 | 21.3 | 76.6 | 2.1 | 7.0 | 0 |
|  | 7 weeks | 50.1 | 1.2 | 98.2 | 0.6 | 22.4 | 74.7 | 2.9 | 7.3 | 0 |
| 40° C. | 4 weeks | n/a | 1.5 | 96.0 | 2.5 | 35.2 | 61.6 | 3.2 | 8.5 | 0 |
|  | 7 weeks | 50.2 | 3.5 | 92.8 | 3.7 | 45.9 | 49.8 | 4.4 | 9.5 | >10 |

The invention claimed is:

1. A pharmaceutical formulation comprising:
   20 to 50 mg/ml of a CEA CD3 bispecific antibody;
   15 to 30 mM L-histidine;
   0.02 to 0.05% (w/v) polysorbate 20;
   120 to 300 mM sucrose; and
   wherein the formulation has a pH of 5.5±0.5,
   (i) a first antigen binding moiety that specifically binds to CD3 and comprises a heavy chain variable region sequence of SEQ ID NO: 7, and the light chain variable region sequence of SEQ ID NO: 8, wherein the first antigen binding moiety is a crossover Fab molecule wherein the constant regions of the Fab light chain and the Fab heavy chain are exchanged;
   (ii) a second and a third antigen binding moiety that specifically binds to CEA, each comprising the heavy chain variable region sequence of SEQ ID NO: 15 and the light chain variable region sequence of SEQ ID NO: 16, wherein the second and third antigen binding moieties are each a conventional Fab molecule; and
   (iii) a human lgG1 Fc domain composed of a first and a second subunit;
   wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the subunit of the Fc domain, and wherein the third antigen binding moiety is fused at the C-terminus of the Fab heavy chain to the N-terminus of the second subunit of the Fc domain.

2. The formulation according to claim 1, comprising:
   50 mg/ml of the CEA CD3 bispecific antibody, 20 mM L-histidine, 0.05% (w/v) polysorbate 20, 230 mM sucrose, and 10 mM methionine, pH 5.5; or
   20 mg/ml of the CEA CD3 bispecific antibody, 20 mM L-histidine, 0.05% (w/v) polysorbate 20, 240 mM sucrose, and 10 mM methionine, pH 5.5.

3. The formulation according to claim 1, comprising:
   50 mg/ml of the CEA CD3 bispecific antibody;
   20 mM L-histidine;
   0.05% (w/v) polysorbate 20;
   230 mM sucrose; and
   10 mM methionine.

4. The formulation according to any one of claims 1, 2, and 3, which is in a liquid form, in a lyophilized form, or in a liquid form reconstituted from a lyophilized form.

5. A method of treatment, comprising administering to a subject who has cancer the formulation of claim 1.

* * * * *